United States Patent [19]
Miwa

[11] Patent Number: 5,946,073
[45] Date of Patent: Aug. 31, 1999

[54] NON-CONTACT TYPE TONOMETER

[75] Inventor: Tetsuyuki Miwa, Aichi, Japan

[73] Assignee: Nidek, Co., Ltd., Gamagori, Japan

[21] Appl. No.: 09/215,211

[22] Filed: Dec. 18, 1998

[30] Foreign Application Priority Data

Dec. 26, 1997 [JP] Japan .................................. 9-369220

[51] Int. Cl.⁶ .................................................. A61B 3/10
[52] U.S. Cl. .......................................... 351/205; 600/399
[58] Field of Search ...................... 351/205, 208; 600/401, 405, 398, 399

[56] References Cited

U.S. PATENT DOCUMENTS

| | | | |
|---|---|---|---|
| 4,996,990 | 3/1991 | Hideshima | 600/401 |
| 5,107,851 | 4/1992 | Yano et al. | 600/405 |
| 5,279,300 | 1/1994 | Miwa et al. | |
| 5,502,521 | 3/1996 | Katou | |

FOREIGN PATENT DOCUMENTS

| | | |
|---|---|---|
| B2-3-51409 | 8/1991 | Japan . |
| A-542109 | 2/1993 | Japan . |
| A-5-56931 | 3/1993 | Japan . |

*Primary Examiner*—George Manuel
*Attorney, Agent, or Firm*—Oliff & Berridge, PLC

[57] ABSTRACT

An non-contact type tonometer is disclosed, wherein a compressed fluid is blown against an examinee's eye for deforming the cornea of the eye and detecting a corneal deformed state to measure intraocular pressure of the examinee's eye. This tonometer controls the blowing of fluid by stopping to compress the fluid when a predetermined condition set with reference to the detected results in a deformation start time of the cornea is fulfilled. This makes it possible to measure the intraocular pressure of the examinee's eye by blowing the fluid at lower pressure, thereby to reducing disagreement to the examinee, without applying excessive pressure of fluid to the examinee's eye.

18 Claims, 3 Drawing Sheets

NON-CONTACT TYPE TONOMETER

BACKGROUND OF THE INVENTION

1. Field of the Invention

The present invention relates to a non-contact type tonometer for measuring intraocular pressure of an examinee's eye to be examined by compressing fluid, blowing the compressed fluid against the cornea of the examinee's eye, and detecting a deformed state in the cornea.

2. Description of Related Art

There is known a non-contact type tonometer which measures intraocular pressure of an examinee's eye by blowing fluid such as air against the examinee's eye, deforming the cornea of the examinee's eye, and detecting a deformed state of the cornea.

As one of such the non-contact type tonometer, there is proposed a mechanism in which plural measurements are continuously made by changing fluid-blowing conditions for second and subsequent measurements based on measurement data on the intraocular pressure of the examinee's eye, obtained after first measurement in which the fluid was blown under a predetermined condition, so that the fluid at excessive high pressure is prevented from being blown unnecessarily against the examinee's eye. This can reduce disagreement applied to the examinee and obtain measurement results with high reliability.

However, in the first measurement, for example, the fluid-blowing is stopped after a predetermined deformed state of the cornea which can provide intraocular pressure is detected. In this case, the fluid at sufficiently low pressure is not always blown against the examinee's eye.

SUMMARY OF THE INVENTION

The present invention has been made in view of the above circumstances and has an object to overcome the above problems and to provide a non-contact type tonometer capable of measuring intraocular pressure of an examinee's eye even by blowing fluid at lower pressure against the examinee's eye thereby to reduce disagreement applied to the examinee.

Additional objects and advantages of the invention will be set forth in part in the description which follows and in part will be obvious from the description, or may be learned by practice of the invention. The objects and advantages of the invention may be realized and attained by means of the instrumentalities and combinations particularly pointed out in the appended claims.

To achieve the purpose of the invention, there is provided a non-contact type tonometer including a fluid blowing device for blowing fluid against a cornea of an eye to be examined; a first detection device for detecting a corneal deformed state caused by the fluid blown from the fluid blowing device; a second detection device for detecting pressure of the fluid blown from the fluid blowing device; and an intraocular pressure calculation device for calculating intraocular pressure of the eye to be examined on a basis of detection results by the first and second detection devices; the non-contact type tonometer including a third detection device for detecting a deformation start time at which the cornea of the eye to be examined starts to be deformed, on a basis of the detection result by the first detection device, a memory for storing a predetermined condition previously determined with reference to the corneal deformation start time, and a control device for causing the fluid blowing device to stop fluid-blowing when the predetermined condition stored in the memory is fulfilled.

In the above non-contact type tonometer of the present invention, the control device controls the fluid-blowing on the basis of the fluid pressure detected by the second detection device without giving excessive fluid pressure against the examinee's eye even in the first measurement, thereby to reduce disagreement to the examinee's eye. Thus reduced disagreement to the examinee's eye can provide a measurement result with high precision.

According to another aspect of the present invention, there is provided a non-contact type tonometer including a fluid blowing means for blowing fluid against a cornea of an eye to be examined; a first detection means for detecting a corneal deformed state caused by the fluid blown from the fluid blowing means; a second detection means for detecting pressure of the fluid blown from the fluid blowing means; and an intraocular pressure calculation means for calculating intraocular pressure of the eye to be examined on a basis of detection results by the first and second detection means; the non-contact type tonometer including a third detection means for detecting a deformation start time at which the cornea of the eye to be examined starts to be deformed, on a basis of the detection result by the first detection means, a memory for storing a predetermined condition previously determined with reference to the corneal deformation start time, and a control means for causing the fluid blowing means to stop fluid-blowing when the predetermined condition stored in the memory is fulfilled.

BRIEF DESCRIPTION OF THE DRAWINGS

The accompanying drawings, which are incorporated in and constitute a part of this specification illustrate an embodiment of the invention and, together with the description, serve to explain the objects, advantages and principles of the invention.

In the drawings.

DETAILED DESCRIPTION OF THE PREFERRED EMBODIMENTS

Figure 1:
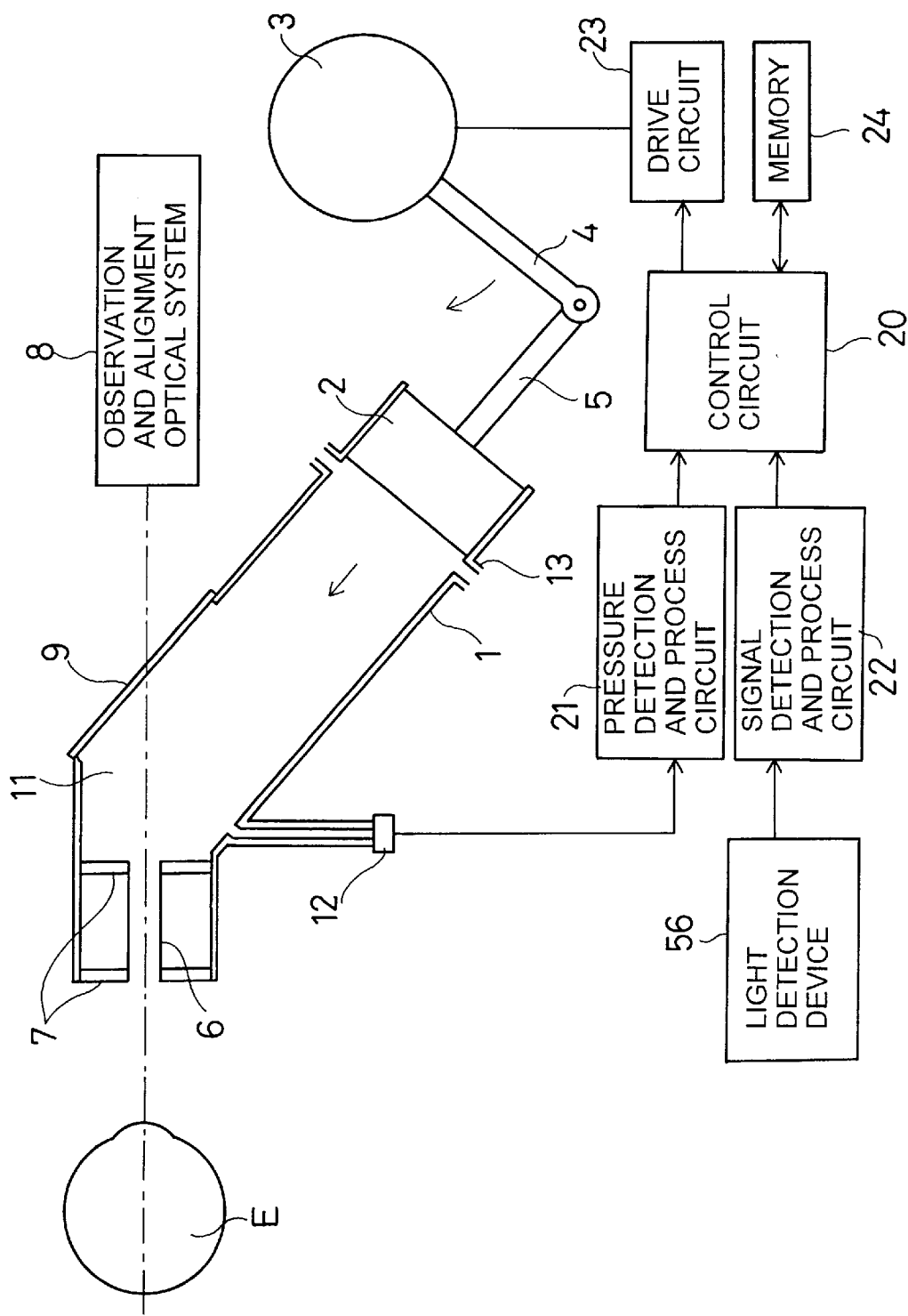
FIG. 1 is a view showing a schematic side structure of an fluid blowing mechanism and a control system for a non-contact type tonometer in an embodiment according to the present invention.

A detailed description of a preferred embodiment of a non-contact type tonometer embodying the present invention will now be given referring to the accompanying drawings. FIG. 1 is a view of a schematic side structure of a fluid blowing mechanism and a control system in the non-contact tonometer.

In FIG. 1, the non-contact tonometer is provided with a cylinder portion 1 for air compression, which is provided inclined to the horizontal line of a tonometer body, a piston 2, and a rotary solenoid 3. This rotary solenoid 3 presses the piston 2 upwardly through an arm 4 and a connecting rod (piston rod) 5 when electric charge (current or voltage) which is driving energy is supplied. Within the cylinder portion 1, there is provided an air compression chamber 11 which communicates with a nozzle 6 through which air is blown outside. The air in the air compression chamber 11 is compressed by the rise of the piston 2, and blown against the cornea of an examinee's eye E through the nozzle 6. The rotary solenoid 3 is provided with a coil spring not shown. When the supplied charge is cut off, the biasing force of the coil spring in a lowering direction causes the raised piston 2 to descend to an initial position.

The non-contact type tonometer is further provided with the following components. A transparent glass plate 7 holds the nozzle 6 and transmits observation light or alignment light. This glass plate 7 also constitutes a side wall of the air compression chamber 11. A transparent glass plate 9 is disposed behind the nozzle 6, and constitutes the rear wall of the air compression chamber 11, transmitting observation light or alignment light. An optical system 8 for observation and alignment, which will be described later, is arranged behind the glass plate 9. There are also provided a pressure sensor 12 for detecting the pressure in the air compression chamber 11, and an air vent hole 13 for reducing the resistance until the initial speed is given to the piston 2, whereby to provide change in pressure, substantially proportional to time, at a rising time of pressure.

The control system of the non-contact type tonometer includes a control circuit 20, a pressure detection and process circuit 21 for processing a signal from the pressure sensor 12, a signal detection and process circuit 22 for processing a signal from a light detection device 56 of a corneal deformation detecting optical system 15 which will be described later, a drive circuit 23 for driving the rotary solenoid 3, and a memory 24 for storing measurement data and others.

Figure 2:
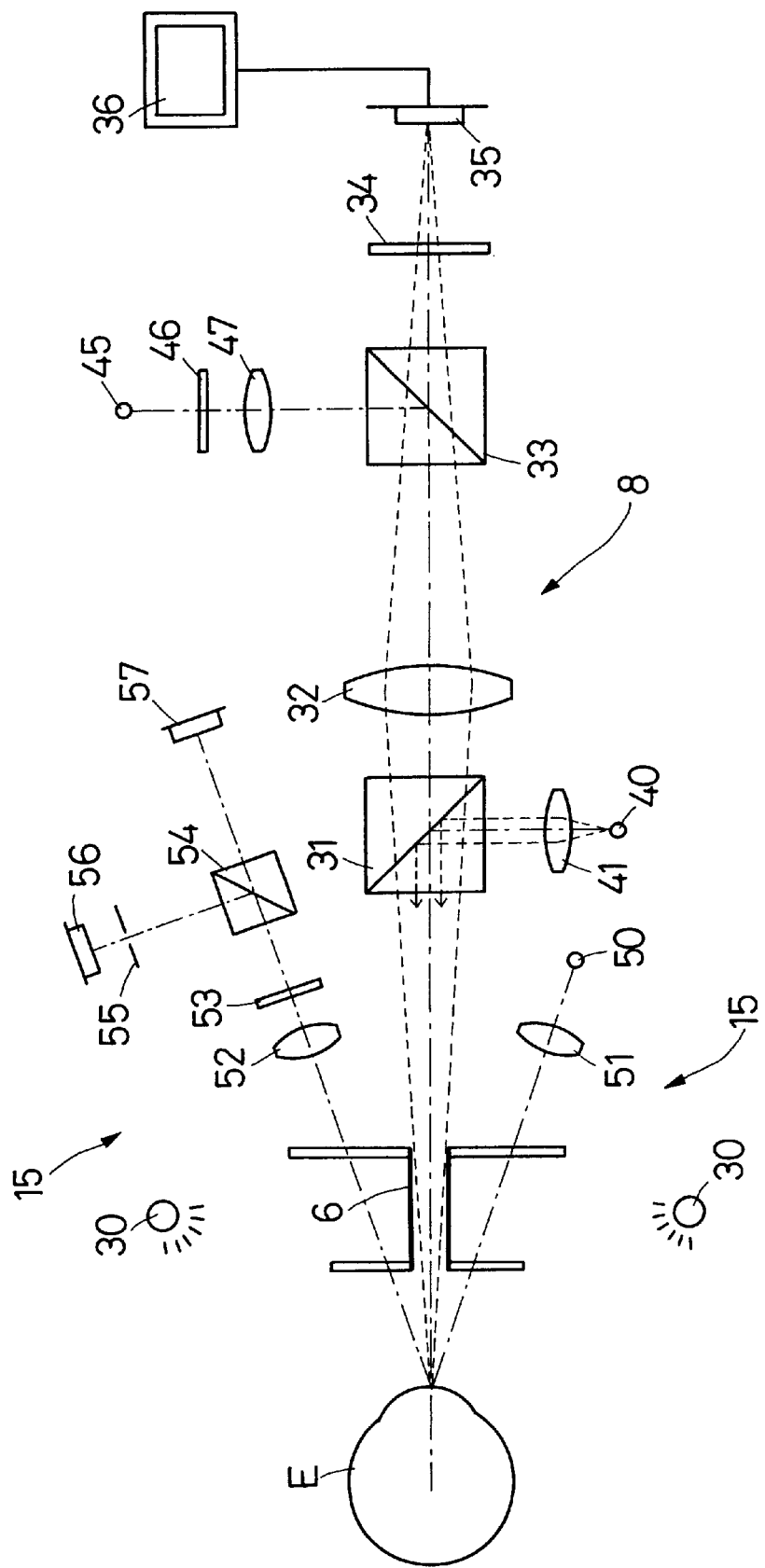
FIG. 2 is a schematic view, as viewed from above, showing the optical system near a nozzle of the fluid blowing mechanism for the non-contact tonometer in the embodiment.

FIG. 2 is a schematic view of a main part of the optical system of the non-contact type tonometer in the embodiment, as viewed from above.

When the examinee's eye E is illuminated by the infrared rays emitted from infrared light sources 30, the image of the eye E is formed on a CCD camera 35 through a beam splitter 31, an objective lens 32, a beam splitter 33, and a filter 34. This filter 34 has the property of passing the light of the light source 30 and that of an alignment light source 40, while not passing the light of an LED 50 for corneal deformation detection which will be mentioned later. The image thus formed on the CCD camera 35 is displayed on a monitor 36.

The alignment light source 40 is an infrared LED for alignment. An infrared light emitted from the LED 40 is reflected by the beam splitter 31, and projected by a projection lens 41 into the cornea of the examinee's eye E. A luminescent spot formed on the corneal apex by the light from the LED 40 is focused on the CCD camera 35 through the components from the beam splitter 31 through the filter 34. The luminescent spot formed on the CCD camera 35 is used for alignment of the non-contact type tonometer with respect to the examinee.

LED 45 is used for projecting a fixation mark. The light in the form of a fixation mark 46 illuminated by the LED 45 passes through a projection lens 47 and reflected by the beam splitter 33 toward the examinee's eye E. An examiner makes a measurement on the examinee's eye E while the examinee stares at the fixation mark 46.

Infrared LED 50 is used for corneal deformation detection. The light emitted from the LED 50 is made into substantial parallel luminous flux by a collimator lens 51, and is projected to the cornea of the eye E. The light reflected by the cornea passes through a light-receiving lens 52, a filter 53 having the property of not passing the light of the light sources 30 and 40, and is reflected by a beam splitter 54. Thus reflected light passes through a pin-hole plate 55 and is received by a light detection device 56. The corneal deformation detection optical system 15 is arranged so that the quantity of light received by the light detection device 56 becomes the maximum when the examinee's eye E is deformed into a predetermined state, e.g., an applanation state.

In the present embodiment, a part of the corneal deformation detection optical system 15 is used in common for a working distance detection optical system. A light emitted from the LED 50, then reflected by the cornea, passes through the light receiving lens 52, the filter 53, the beam splitter 54 and is received by a one-dimensional detecting element 57. The control circuit 20 obtains working distance information on the basis of the position at which the light is received in the detecting element 57.

The operation of the non-contact type tonometer constructed as above will be described hereinafter.

The examiner places the examinee's eye E at a predetermined position, and handles a joystick not shown to perform alignment in accordance with the alignment information displayed on the monitor 36. For alignment adjustment in up-and-down and right-and-left directions, the examiner adjusts the joystick so as to place the luminescent spot in a predetermined positional relation to a reticle (not shown) displayed on the monitor 36. For alignment adjustment in a working distance, the examiner adjusts the joystick in accordance with a distance index displayed on the monitor 36, representing the working distance information obtained from the one-dimensional detection element 57. For the details of the alignment adjustment, refer to U.S. Pat. No. 5,502,521 by the present applicant. It is to be noted that an automatic alignment can be made by moving a measuring part of the non-contact type tonometer on the basis of the detection information of an alignment index.

Upon completion of the alignment, the examiner presses a measurement start switch (or the control circuit 20 automatically sends a measurement start signal in accordance with a signal from the alignment optical system) to start measurement. On receipt of the measurement start signal, the control circuit 20 operates to supply electric charge as driving energy capable of actuating the rotary solenoid 3 thereto through the driving circuit 23 to drive the rotary solenoid 3.

The supply of electric charge to the rotary solenoid 3 causes the rise of the piston 2, compressing the air in the air compression chamber 11. The compressed air is blown against the cornea of the examinee's eye E through the nozzle 6. The cornea is gradually deformed by the compressed air thus blown. The reflected light, by the cornea, of light projected from the LED 50 is received by the light detection device 56 to detect the deformed state of the cornea by means of the light detection device 56.

Figure 3:
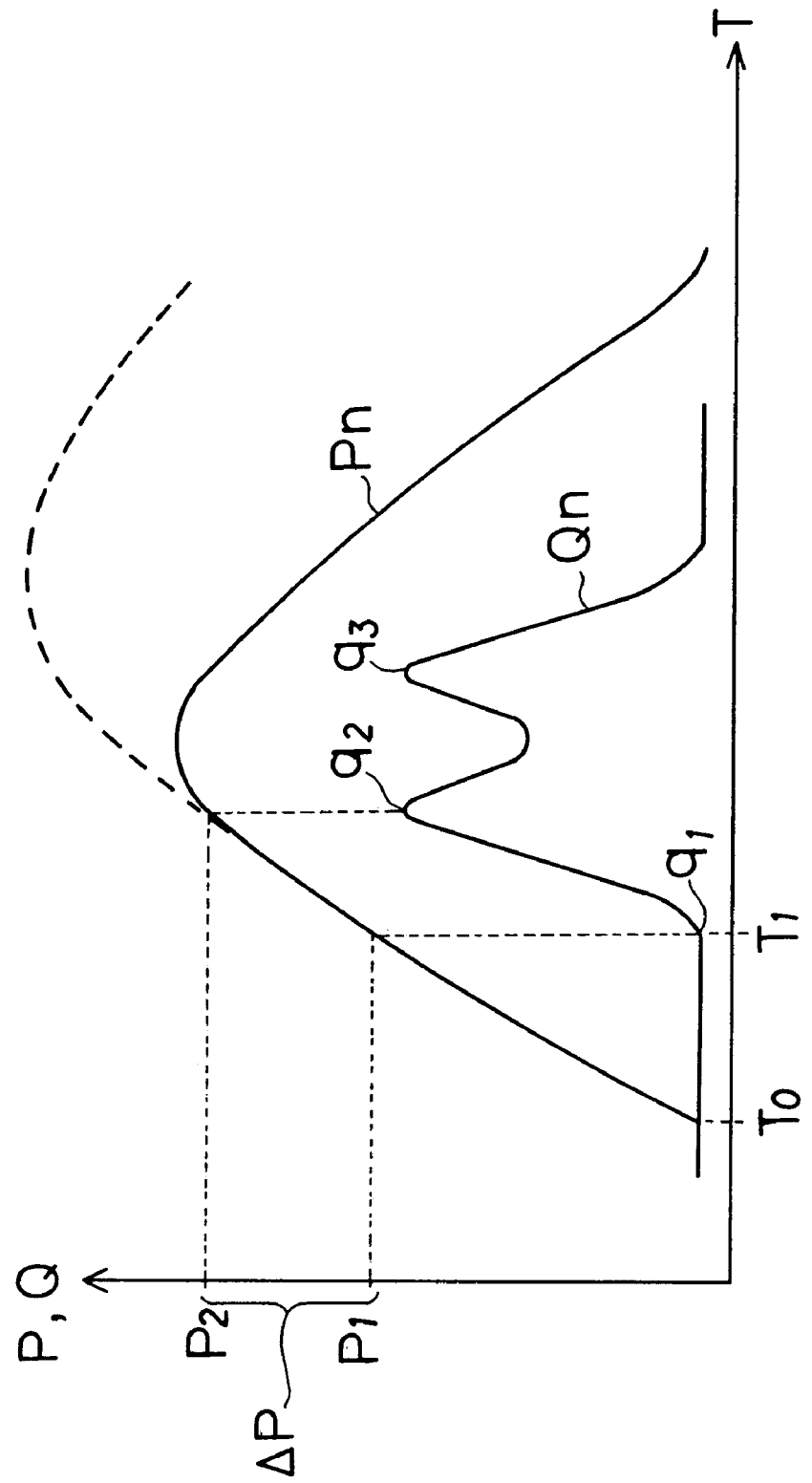
FIG. 3 is a time series diagram showing changes in pressure in a cylinder during piston driving, a quantity of received light in a light detection device for detecting a deformed state of a cornea of an examinee's eye, and supplied voltage to a piston driving device.

FIG. 3 is a time series diagram showing changes in pressure Pn detected by the pressure sensor 12 and deformation signal Qn representative of the quantity of received light in the light detection device 56.

When the piston 2 is raised due to the driving of the rotary solenoid 3, the air in the air compression chamber 11 is compressed, and the pressure Pn detected by the pressure sensor 12 substantially linearly increases with the rise of the piston 2. Similarly, the pressure of the compressed air increases, when the compressed air is blown against the eye E through the nozzle 6.

Accordingly, the cornea of the eye E starts to be deformed by the compressed air. On commencement of deformation of the cornea, the quantity of received light in the light detection device 56 begins to extremely increase, so that the deformation signal Qn based on the received light quantity begins to suddenly increase. The control circuit 20 detects a first pressure value P1 at the rising point q1 when the deformation signal suddenly rises, and stores it in the memory 24.

The control circuit 20 continuously or intermittently obtains the pressure in the air compression chamber 11 by receiving the signal from the pressure sensor 12. When the control circuit 20 obtains a third pressure value P2 which is changed from the first pressure value P1 by a second pressure value $\Delta P$ which is previously set as an increment value, the control circuit 20 causes the drive circuit 23 to stop the supply of electric charge to the rotary solenoid 3.

The increment value $\Delta P$ is determined to a value including a tolerance in consideration of a factor responsible for variations in intraocular pressure so that peak signals q2 and q3 for detection of the corneal deformation may be detected. The increment value $\Delta P$ may be changed depending on the rising point q1 (which indicates the time from a measurement start time T0 to a time T1 corresponding to the point q1) of the deformation signal Qn. That is, the start time of the corneal deformation varies with individual intraocular pressures of eyes to be examined. In the case of the examinee's eye having high intraocular pressure, the cornea thereof is not deformed until the air blowing pressure increases to a predetermined level, and therefore the deformation start time becomes late. To the contrary, in the case of low intraocular pressure, the cornea is deformed even when the air blowing pressure is low, and therefore the deformation start time becomes early. For example, if the intraocular pressure is low, the time from the supply of electric charge to the rotary solenoid 3 to the rising point q1 becomes short (the point q1 is moved leftward in the FIG. 3), and the necessary time from the rising point q1 to the peak point q2, i.e., the time required until the cornea is deformed into a predetermined deformed state, becomes short. Accordingly, the increment value $\Delta P$ is set to a small value. On the other hand, if the intraocular pressure is high, the time required until the cornea is deformed into a predetermined deformed state becomes long, and the increment value $\Delta P$ is set to a large value. Thus, the compressed air can be blown at more appropriate pressure according to the intraocular pressure of the examinee's eye.

The increment value $\Delta P$ may be changed and determined on the basis of the first pressure value P1 at the rising point q1 of the deformation signal Qn. Specifically, the cornea of the examinee's eye having low intraocular pressure begins to be deformed by the air blown at low pressure, when the detected first pressure value P1 is small. If the detected pressure value P1 is small (namely, low intraocular pressure), the necessary time from the rising point q1 to the peak q2 becomes short, and thus $\Delta P$ is set to a small value. If the intraocular pressure is high, requiring the long time until the cornea thereof is deformed into a predetermined deformed state, and the increment value $\Delta P$ is set to a large value.

Although the piston 2 is raised by an inertia force even after the supply of electric charge to the rotary solenoid 3 is stopped, the biasing force caused by the coil spring in the lowering direction is exerted on the piston 2. The biasing force of the coil spring and the gravity applied to the piston 2 attenuate the speed of the piston 2 to stop it once, and thereafter to lower. Thus, the pressure in the air compression chamber 11 increases to a somewhat higher value than the third pressure value P2, and thereafter lowers. The deformation signal Qn, on the other hand, reaches a peak when the piston 2 is caused to rise by an inertia force, and thereafter lowers once and reaches a peak again, finally lowers. The points q2 and q3 where the deformation signal Qn reaches a peak indicate that a predetermined deformed state of the cornea has been attained. The control circuit 20 obtains the intraocular pressure on the basis of the peak signal at the first peak point q2. The intraocular pressure of the examinee's eye E can be obtained on the basis of the gas pressure directly or indirectly detected when the cornea of the examinee's eye has been deformed into a predetermined state by compressed gas blown against it. For the details of the measurement of intraocular pressure, refer to U.S. patent application Ser. No. 07/933,303 and U.S. Pat. No. 5,279,300 by the present applicant.

Consequently, the non-contact type tonometer in the embodiment can make the measurement of intraocular pressure by the use of the lower blowing pressure of air to be blown against the examinee's eye, as compared with the case where the supply of electric charge to the rotary solenoid 3 is stopped after a predetermined deformed state of the cornea has been detected.

It is arranged that, in second and following measurements, the supply of electric charge to the rotary solenoid 3 is controlled on the basis of a separated condition between the peak signals q2 and q3 for detection of the corneal deformation, detected in the first measurement, and the time until the fluid pressure reaches the maximum, thereby to blow compressed air at the optimum pressure against the examinee's eye (refer to U.S. Pat. No. 5,279,300).

The present invention may be embodied in other specific forms without departing from the spirit or essential characteristics thereof. For instance, time may be used instead of the increment value $\Delta P$.

The foregoing description of the preferred embodiment of the invention has been presented for purposes of illustration and description. It is not intended to be exhaustive or to limit the invention to the precise form disclosed, and modifications and variations are possible in light of the above teachings or may be acquired from practice of the invention. The embodiment chosen and described in order to explain the principles of the invention and its practical application to enable one skilled in the art to utilize the invention in various embodiments and with various modifications as are suited to the particular use contemplated. It is intended that the scope of the invention be defined by the claims appended hereto, and their equivalents.

What is claimed is:

1. A non-contact type tonometer including a fluid blowing device for blowing fluid against a cornea of an eye to be examined; a first detection device for detecting a corneal deformed state caused by the fluid blown from the fluid blowing device; a second detection device for detecting pressure of the fluid blown from the fluid blowing device; and an intraocular pressure calculation device for calculating intraocular pressure of the eye to be examined on a basis of detection results by the first and second detection devices; the non-contact type tonometer including:

a third detection device for detecting a deformation start time at which the cornea of the eye to be examined starts to be deformed, on a basis of the detection result by the first detection device;

a memory for storing a predetermined condition previously determined with reference to the corneal deformation start time; and a control device for causing the fluid blowing device to stop fluid-blowing when the predetermined condition stored in the memory is fulfilled.

2. The non-contact type tonometer according to claim 1, wherein the predetermined condition is a condition that a fluid pressure value detected by the second detection device comes to a third pressure value obtained by adding a second pressure value which is a predetermined increment to a first fluid pressure value at the corneal deformation start time.

3. The non-contact type tonometer according to claim 2, wherein the second pressure value which is a predetermined increment is determined so that, when the first detection device detects a peak signal representative of an applanation state of the cornea, fluid pressure detected by the second detection device comes to the third pressure value.

4. The non-contact type tonometer according to claim 2, wherein the second pressure value is determined on a basis of a period of time from a measurement start time to the corneal deformation start time detected by the third detection device.

5. The non-contact type tonometer according to claim 4, wherein, when the period of time is short, the second pressure value is set to a small value.

6. The non-contact type tonometer according to claim 4, wherein when the period of time is long, the second pressure value is set to a large value.

7. The non-contact type tonometer according to claim 2, wherein the second pressure value is determined depending on the first pressure value obtained at the corneal deformation start time.

8. The non-contact type tonometer according to claim 7, wherein, when the first pressure value is small, the second pressure value is set to a small value.

9. The non-contact type tonometer according to claim 7, wherein, when the first pressure value is large, the second pressure value is set to a large value.

10. A non-contact type tonometer including a fluid blowing means for blowing fluid against a cornea of an eye to be examined; a first detection means for detecting a corneal deformed state caused by the fluid blown from the fluid blowing means; a second detection means for detecting pressure of the fluid blown from the fluid blowing means; and an intraocular pressure calculation means for calculating intraocular pressure of the eye to be examined on a basis of detection results by the first and second detection means; the non-contact type tonometer including:

a third detection means for detecting a deformation start time at which the cornea of the eye to be examined starts to be deformed, on a basis of the detection result by the first detection means;

a memory for storing a predetermined condition previously determined with reference to the corneal deformation start time; and a control means for causing the fluid blowing means to stop fluid-blowing when the predetermined condition stored in the memory is fulfilled.

11. The non-contact type tonometer according to claim 10, wherein the predetermined condition is a condition that a fluid pressure value detected by the second detection means comes to a third pressure value obtained by adding a second pressure value which is a predetermined increment to a first fluid pressure value at the corneal deformation start time.

12. The non-contact type tonometer according to claim 11, wherein the second pressure value which is a predetermined increment is determined so that, when the first detection means detects a peak signal representative of an applanation state of the cornea, fluid pressure detected by the second detection means comes to the third pressure value.

13. The non-contact type tonometer according to claim 11, wherein the second pressure value is determined on a basis of a period of time from a measurement start time to the corneal deformation start time detected by the third detection means.

14. The non-contact type tonometer according to claim 13, wherein, when the period of time is short, the second pressure value is set to a small value.

15. The non-contact type tonometer according to claim 13, wherein when the period of time is long, the second pressure value is set to a large value.

16. The non-contact type tonometer according to claim 11, wherein the second pressure value is determined depending on the first pressure value obtained at the corneal deformation start time.

17. The non-contact type tonometer according to claim 16, wherein, when the first pressure value is small, the second pressure value is set to a small value.

18. The non-contact type tonometer according to claim 16, wherein, when the first pressure value is large, the second pressure value is set to a large value.

* * * * *